United States Patent [19]

Dellinger

[11] 4,284,405
[45] Aug. 18, 1981

[54] ORTHODONTIC APPLIANCE METHOD OF TREATMENT AND MANUFACTURE

[76] Inventor: Eugene L. Dellinger, 1326 Old Lantern Trail, Fort Wayne, Ind. 46825

[21] Appl. No.: 98,908

[22] Filed: Nov. 30, 1979

[51] Int. Cl.³ .............................................. A61C 3/00
[52] U.S. Cl. ........................................ 433/24; 433/3; 433/9; 433/8
[58] Field of Search ..................... 433/24, 9, 8, 10, 3

[56] References Cited

U.S. PATENT DOCUMENTS

| | | | |
|---|---|---|---|
| 3,203,098 | 8/1965 | Petraitis | 433/23 |
| 3,345,745 | 8/1967 | Müller | 433/9 |
| 3,421,221 | 1/1969 | Silverman et al. | 433/23 |
| 3,439,421 | 4/1969 | Perkowski | 433/24 |
| 3,521,355 | 7/1970 | Pearlman | 433/3 |
| 3,738,005 | 6/1973 | Cohen et al. | 433/3 |
| 3,787,976 | 1/1974 | Cohen | 433/3 |
| 3,936,939 | 2/1976 | Faunce | 433/9 |
| 4,014,096 | 3/1977 | Dellinger | 433/24 |
| 4,160,322 | 7/1979 | Frazier | 433/24 |

Primary Examiner—Gene Mancene
Assistant Examiner—John J. Wilson
Attorney, Agent, or Firm—Gust, Irish, Jeffers & Hoffman

[57] ABSTRACT

An orthodontic method and appliance for treating malocclusion comprising the steps of forming a model of the patient's teeth in the form of a dental arch with the replicas of the teeth in idealized locations, establishing on the labial and buccal surfaces of the replicas locations which conjointly define an idealized dental arch configuration, providing on each selected surface at the established location an orienting embossment, and forming onto the crown and surface, including such embossment, in intimate conforming engagement, of each selected replica a plate-like fixture which has an exterior provided with a locating boss corresponding to the shape of the embossment and a mounting surface surrounding the boss which corresponds to the replica surface. A bracket is provided having a socket which intimately fits over the boss thereby to be oriented with respect to the fixture. The fixture is transferred from the replica to the corresponding tooth in the patient's mouth with the custom formed base portion of a fixture which underlies the boss being suitably bonded to the tooth. The remaining portion of the fixture, principally that which overlies the crown, is then separated or broken away leaving the base portion of the fixture with the attached bracket bonded to the tooth.

34 Claims, 8 Drawing Figures

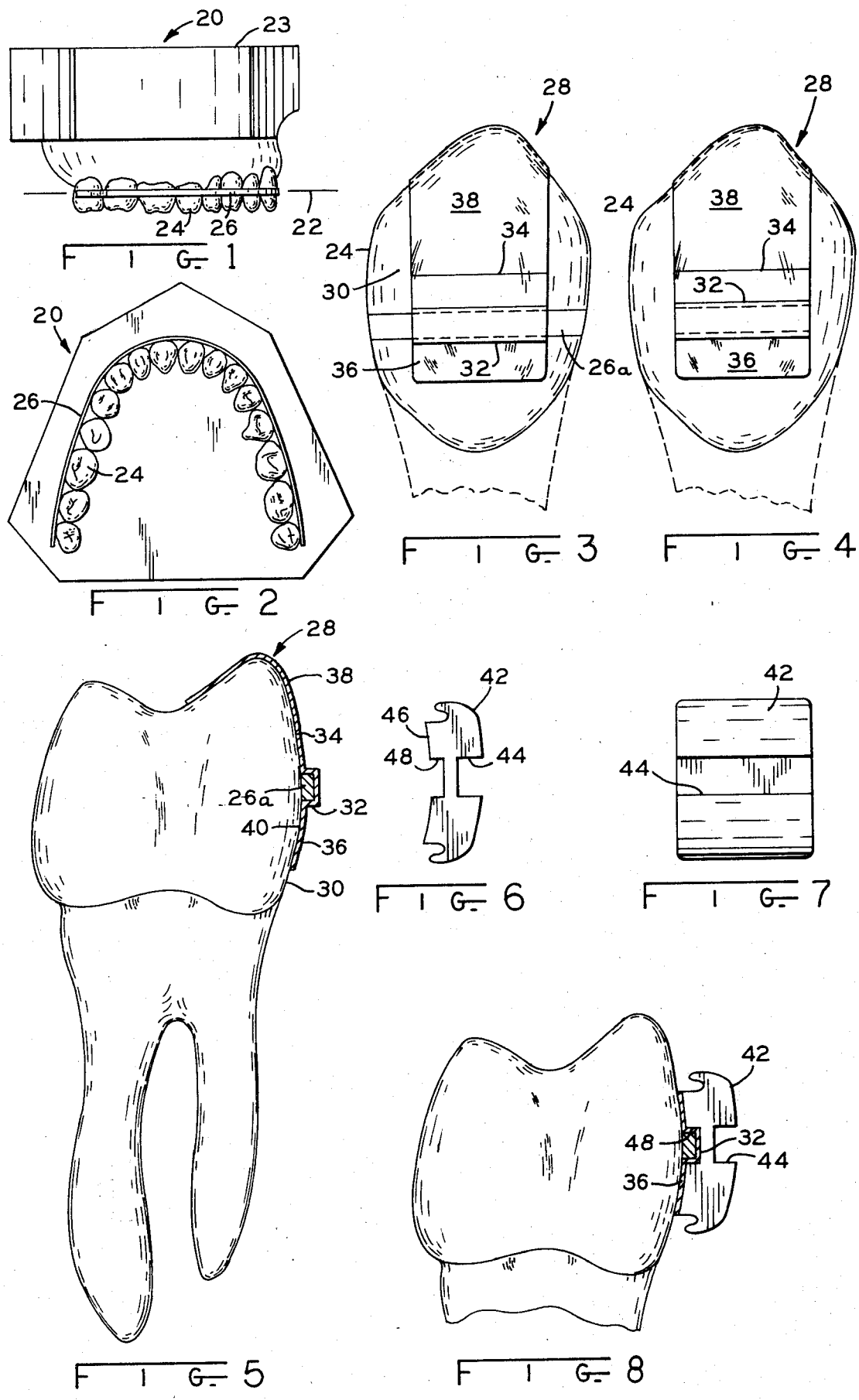

ORTHODONTIC APPLIANCE METHOD OF TREATMENT AND MANUFACTURE

BACKGROUND OF THE INVENTION

1. Field of the Invention

The present invention relates to orthodontics and more particularly to a method and apparatus for determining bracket position initially and throughout the period of treatment in accordance with a predetermined treatment plan.

2. Description of the Prior Art

Known prior art procedures are available to the orthodontist ideally to finish treatment with a coplanar arch wire having no buccal-lingual steps or other adjustment factors. Examples are disclosed in Dellinger U.S. Pat. Nos. 4,014,096 and Schinhammer 3,949,478. Of importance in following such procedures is the precise and correct placement of brackets upon the teeth, achieved by means of idealized laboratory models used to predetermine such placement. With reference to the Dellinger patent, band mounted brackets are finish fabricated on the model to conform to an idealized coplanar arch wire shape, while in the Schinhammer patent prefabricated brackets are ideally located on the model and eventually incorporated into a transfer mask conforming to the malocclusion for placement on the patient's teeth to initiate treatment. Further with respect to the Dellinger patent, an alternative is provided wherein a bracket-locating device is initially formed with reference to the estimated location of a bracket slot which is subsequently cut into a blank bracket mounted on the laboratory model. The bracket-locating device is then used to position the bracket on the tooth utilizing the post-formed slot. Should the estimated location be other than coincident with the postformed slot, error in bracket placement results. Thus, the accuracy of placement depends upon the accuracy of the estimated slot location, an inexact technique at best.

In following the foregoing procedures with particular reference to direct bonding, it is intended to obtain the precise and correct placement of brackets on the teeth such that finished treatment with a coplanar arch wire may be achieved; however, during the relatively long period of treatment should there be a requirement to replace a bracket for some reason, such as a bracket having been lost or damaged, replacement in the same, precise, laboratory established position once again becomes an estimate and a matter of practitioner judgment and skill. Once bracket replacement is inaccurately performed, the original purpose of finish treatment with a coplanar arch wire, or an arch wire of desired configuration, can no longer be realized, thus diminuting the efficacy of the originally intended procedure.

Consequently, in order for the practitioner to obtain the desired end result, some method and apparatus are needed by means of which the precise and correct placement of brackets on the teeth can not only be achieved at the outset of treatment but also during treatment. Finish treatment could then be performed by means of a pre-configured arch wire, in the usual instance the preferred form being coplanar. By satisfying this need, the practitioner has complete control of the variables normally involved with the usual guesswork and corresponding judgment factors being eliminated. Also, this would result in reducing the degree of skill and time required on the part of the practitioner and in improved patient comfort during treatment.

SUMMARY OF THE INVENTION

The present invention relates to a technique in which the slots of the brackets on the patient's teeth upon completion of treatment are oriented to a pattern predetermined in a set of occluded models, the pattern being of coplanar, arch form. When treatment of the patient is completed, the bracket slots are coplanar and the teeth are aligned according to the idealized model. While a coplanar pattern is preferred, the pattern may include buccal-lingual steps as well as deviations from a common plane. When treatment is completed, the bracket slots define a geometric pattern corresponding to the predetermined geometry.

In the method of this invention, malocclusion is treated according to the steps of forming a model of the patient's teeth in the shape of a dental arch with the replicas of the teeth being disposed in idealized locations, establishing on the labial and buccal surfaces of selected ones of said replicas locations for the mounting of brackets, providing on each selected surface at the established location an orienting embossment, forming onto the crown and surface, including the embossment, and intimate conforming engagement, of each selected replica a plate-like fixture which has an exterior provided with a locating boss corresponding to the shape of the embossment and a mounting surface surrounding the boss which corresponds to the replica surface, transferring each fixture to the corresponding tooth in the patient's mouth, adhering the portion of the fixture immediately surrounding the boss to the tooth, and separating from the tooth the crown portion of the fixture leaving the remainder including the boss and the surrounding portion in the form of a custom formed mounting base for a bracket.

In the method of fabricating an orthodontic appliance for use in repositioning one or more teeth in a patient's mouth, the steps include forming a model of the patient's teeth in the shape of a dental arch with the replicas of the teeth in idealized locations, establishing on the labial and buccal surfaces of selected ones of the replicas locations for the mounting of brackets, providing on each selected surface at the established location an orienting embossment, and forming onto the incisal edge and surface including such embossment, in intimate conforming engagement, of each selected replica a plate-like fixture which has an exterior provided with a locating boss corresponding to the shape of the embossment and a mounting surface surrounding the boss which corresponds to the replicas surface.

Also provided in accordance with this invention is apparatus for locating a bracket on the labial or buccal surface of the tooth comprising a plate-like fixture having a shape which conforms to a portion of the crown and labial or buccal surface of the tooth. The labial or buccal portion of the fixtures serves as a mounting base for a bracket and has a locating boss thereon. The crown portion of the fixture serves to locate the mounting base on the aforesaid surface of a patient's tooth. Used in conjunction with the plate-like fixture is a bracket having a bottom surface provided with a socket therein. The socket is so sized and shaped to have a mating fit with the boss while said bottom surface is engaged with the base. The bracket once assembled to the base is then secured in place thereto.

It is an object of this invention to provide a method and apparatus which facilitates treatment of malocclusion.

It is another object of this invention to provide a method and apparatus which will enable a practitioner to maintain a predetermined plan of treatment throughout the period of treatment.

It is yet another object of this invention to provide a method for fabricating a fixture for use in locating and attaching a bracket to a tooth in a predetermined location.

Still another object of this invention is to provide a unique bracket construction whereby a bracket may be easily assembled and bonded to a tooth in a predetermined location.

The above-mentioned and other features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

FIG. 1 is a side elevation of a model of a patient's teeth in the shape of a dental arch with the replicas of the teeth in idealized location and an orienting bar thereon;

FIG. 2 is a plan view thereof;

FIG. 3 is a partial front elevation of one of the replicas of a tooth in the model of the preceding figures with a plate-like fixture attached thereto;

FIG. 4 is a similar view but of the same fixture of FIG. 3 transferred to a corresponding tooth of the patient;

FIG. 5 is a side view of the patient's tooth of FIG. 4 with the plate-like fixture mounted thereon;

FIG. 6 is an end view of the bracket which is adapted to fit onto the fixture of FIG. 5;

FIG. 7 is a front elevation of the bracket of FIG. 6; and

FIG. 8 is a view similar to FIG. 5 but with the bracket and base bonded to the tooth and the crown portion of the fixture removed.

DESCRIPTION OF THE ILLUSTRATED EMBODIMENTS

In practicing the present invention, an idealized model of the patient's teeth is produced in the laboratory in accordance with the disclosure in Dellinger U.S. Pat. No. 4,014,096 which is incorporated herein by reference. Briefly, an impression of a patient's teeth is taken and casting material is poured into the impression for the purpose of obtaining a working cast or model. The casting material may be in the form of plastic, an example being acrylic. The cast teeth or replicas are then sectioned from the working cast by any suitable method, such as cutting, and reset into a soft plastic media, such as wax, in an ideal or overtreated position as determined by the practitioner. The model thus created is in the form of an ideal occlusion or an ideal overtreatment of the original malocclusion as determined by the practitioner, this model being the idealized model referred to hereinabove. Liquid acrylic, for example, is flowed around the stems of the sectioned replicas, which upon hardening, provides a rigid model of the idealized dental arch which may be handled as an integrated unit, referred to in the aforesaid U.S. Pat. No. 4,014,096 as the master matrix unit. Such a unit is indicated by the numeral 20 in FIGS. 1 and 2. The unit or model 20 is provided with a flat bottom surface which is rested on a flat, horizontal surface which serves as a reference from which height measurements are taken.

A coplanar line or mark 22 lying in a plane parallel to the flat surface 24 on the model 20 is drawn on the replicas 24 of the teeth. The position of this line 22 on each replica 24 is selected by the clinician to coincide with the desired location of the slot in a bracket of the direct bond type. Thus, the line 22 around the entire dental arch will correspond to the shape of an arch wire, preferably smoothly curvilinear and coplanar, to be used in the final stages of treatment. Such an arch wire is disclosed in the aforesaid U.S. Pat. No. 4,014,096. Other line patterns determined by the arch wire shape desired can also be used.

In the following is described the method of constructing a bracket-orienting module or fixture which also serves in part as a custom formed base portion of a bracket to be directly bonded onto a tooth. Referring first to FIGS. 1 and 2, a coplanar arch shaped bar 26 is engaged and adhered to the labial and buccal surfaces of the replicas 24 in registry with the line or plane 22. The bar 26 in one form may be rectangular in cross-section. An impression is made from the model 20 with the bar 26 thereon and from this another working cast is made or acrylic or the like plastic which now contains a duplicate of not only the replicas 24 but also the bar 26. Plate-like metal fixtures, such as the one generally indicated by the numeral 28 are now formed over all or selected ones of the replicas 24. Each fixture 28 preferably is of thin gauge metal and in part is formed over the crown or incisal edge of the replica 24 and onto the labial surface 30 in intimate conformity therewith. A suitable method of forming the fixture 28 is by electroplating directly onto the working cast, those portions of the cast which are not to be plated being suitably masked in accordance with usual techniques thereby limiting the plating to discrete portions of the selected replica 24. As shown more clearly in FIGS. 3 and 5, the fixture 28 is made of a width corresponding to that of the base of a conventional bracket and a length which extends from near the gum line longitudinally across the labial surface and over the incisal edge or crown for a suitable distance as will appear from the description that follows. In the process of the electroplating, the fixture 28 also forms over the duplicate 26a of the bar 26 thereby providing a rectangular boss 32 which is elongated and extends transversely of the labial surface 30.

A section of the fixture 28 is weakened along a transverse line 34 by scoring with a knife, indenting or the like, for a purpose to be explained later. This line 34 divides the fixture 28 into essentially two sections, a portion 36 characterized as a custom formed, bracket-mounting base and another portion 38 which fits over the incisal edge and serves in orienting the base 36 relative to the incisal edge. The electroplating is controlled to provide a thickness in the fixture of from about 0.010 to 0.020 inches. Other thicknesses may be used without departing from the scope of this invention as will appear from the following description.

Thus formed, the fixture 28 intimately conforms to the peculiar irregularities whereby the base 36 may be said to be custom fitted to the curvature and irregularities of the labial surface of the tooth.

The formation of the fixtures 28 may be performed on the individual replicas after sectioning from the model or alternatively may be formed simultaneously on a plurality of selected replicas or the model itself.

Alternative to electroplating is the method of magnetically forming discrete segments of sheet metal of suitable thickness over the incisal edge and labial surface of the replica as taught in U.S. Pat. No. 4,015,333. In this event, it is preferred that the tooth replicas with the embossments 26a thereon be sectioned from the model before the magnetic forming operation is performed. This will also result in producing a fixture 28 in the same form as is obtained by electroplating.

Following formation of the fixtures 28, they are removed from the replicas 24 by using a suitable release agent or dissolving away the replica, it being important that the shape of the fixture 28 be preserved.

The fixtures 28 are now ready for installation on the corresponding teeth in the patient's mouth. Each fixture 28 is placed on the corresponding tooth in the patient's mouth in the same position of engagement as it was formed on the replica and there it is adhered in place using a suitable bonding agent. One suitable procedure is to apply the usual bonding cement to the undersurface 40 of the mounting base 36. This mounting base portion 36 will thus bond to the labial surface of the tooth depending upon its location as determined by the engagement of the fixture portion 38 with the incisal edge and the mating contour of the base portion. Once the cement has suitably hardened, the portion 38 is removed from the tooth by separating or breaking away from the base portion 36 along the weakened section 34. This then leaves the base 36 bonded to the tooth in precisely the same location as on the replica, the base 36 being custom fitted to the curvature and irregularities of the labial surface.

Next, a bracket indicated by the numeral 42 is fabricated to have the usual wire-attaching slot 44. The bottom of the bracket, however, is formed with a surface 46 having centrally located a socket 48 sized and shaped to fit slidably over and mate with the boss 32. Preferably, the wire-receiving slot 44 and the socket 48 are juxtaposed and parallel. Bracket 42 is fitted over the boss 32 with the bottom surface 46 engaging the external surface of the base 36, as shown in FIG. 8. The bracket 42 is secured to the base 36 by some suitable means such as soldering, cementing or the like. The combination of the bracket 42 and the base 36 are now securely bonded to the patient's tooth for having attached thereto the usual arch wire.

If desired, the bracket 42 may be assembled and secured to the base portion 36 of the fixture 28 prior to mounting on the patient's tooth. In fact, duplicate fixture—bracket assemblies may be fabricated to be used by the practitioner in the event the original needs to be replaced.

In an alternative method, the bar 26 may be formed of a suitable plastic adhered to the replicas 24. The fixtures 28 may thus be electroplated, as explained, on the model or the replicas sectioned therefrom. This technique thus eliminates the requirement of making a second, ideal model.

While the coplanar bar 26 serves as a convenient method of orientation, individual embossments, one for each tooth may be employed, each being precisely located on the line 22. By using an orthogonal or some dissimilar orienting shape, the fixture formed thereover will provide an orienting boss which will receive a companion socket in the bracket. The bracket will thus be positioned properly without need of any further adjustment.

If desired, prior to mounting on the tooth, the cavity portion of the embossment 32 may be filled with a suitable liquid plastic which hardens flush with the undersurface 40. This serves to add rigidity and to provide more surface area for bonding of the base to the tooth.

The brackets 42 may be assembled to the fixtures 28 while the latter are still mounted on the model. By reason of the juxtaposition of the slots 44 with the respective bosses 32, the slots conjointly will be coplanar and will define a smooth, curved arch wire shape. An arch wire may be thus formed coplanar and smoothly curved to fit the slots, this same wire being useable in final treatment of the patient. While a coplanar geometry is usually preferred, there may be some cases which would require a different shape. This can be determined beforehand on the model by the practitioner and the brackets and slots arranged correspondingly. Also, the slots may be so located and angled to provide for a desired overtreatment as the practitioner may decide upon.

Alternative to the formation of the embossments 26a and the resulting bosses 32, the coplanar bar 26 may be omitted. Instead, the fixtures 28 may be initially formed over the replicas on the model with no embossments thereon. Afterwards a coplanar line, like line 22, may be drawn across the fixtures. Individual bosses of suitable orienting shape such as cubical or rectangular may be affixed to respective fixtures by soldering or cementing in registry with the line 22. The resulting structure will thus correspond to that formed by using the embossing bar 26, assuming the same boss geometry is used.

Still further, it may be desired to omit entirely the bosses for bracket mounting. In this event, the brackets would be secured to the respective fixtures in registry with the preestablished line locations while being oriented by means of a coplanar arch wire fitted in the bracket slots.

While the preceding disclosure refers to the use of bosses, other bracket-orienting arrangements may be used such as indentations or apertures in the fixtures. Such indentations or apertures would be located precisely the same as the bosses 32 and would have orienting shapes such as orthogonal, triangular, etc. The bracket bases would correspondingly be formed with mating projections or embossments such that the brackets could be assembled to the fixtures and secured thereto in precisely the same locations and orientation as in the preceding embodiments. Summarizing, the bosses, indentations and apertures constitute bracket orienting irregularities on the fixtures which mate with corresponding portions on the brackets for locating and orienting the latter.

By utilizing the method and apparatus of this invention, brackets may be direct bonded to the teeth in a patient's mouth in precise and correct positions which will enable finishing treatment by means of a pre-configured arch wire which is coplanar without any buccal-lingual steps. However, the locations established on the replicas and the arch wire may be other than coplanar and provided with such steps as may be predetermined by the practitioner, the fixtures being fabricated according to the predetermined arch wire shape. During treatment, should any bracket or base become dislodged or damaged, it can be replaced in precisely the same position as the original by utilizing another fixture identical to the first.

Since all of the fixtures are prefabricated in a laboratory in accordance with a predetermined plan of treatment on an idealized model, much of the guesswork and many of the judgment factors involved conventionally in the selection and location of brackets on the part of a practitioner are eliminated, the locations of the brackets on the teeth being provided for the practitioner by means of the fixtures which are fabricated to correspond to the shape of the arch wire used for final treatment. When treatment is finished, the patient's teeth will occupy positions according to the idealized model, since the same arch wire as fitted to the model is used for final treatment. With the arch wire being coplanar, the slots of the brackets on the model and in the patient's mouth upon completion of treatment will also be coplanar.

While there have been described above the principles of this invention in connection with a specific method and apparatus, it is to be clearly understood that this description is made only by way of example and not as a limitation to the scope of the invention.

What is claimed is:

1. The method of fabricating an orthodontic appliance for use in repositioning one or more teeth in a patient's mouth, comprising the steps of:
   (a) forming a model of the patient's teeth in the shape of a dental arch with the replicas of the teeth in idealized locations,
   (b) establishing on the labial or buccal surfaces of selected ones of said replicas locations for the mounting of brackets,
   (c) providing on each selected surface at the established location an orienting embossment,
   (d) and forming onto the incisal edge and surface, including such embossment, in intimate conforming engagement, of each selected replica a plate-like fixture which has an exterior provided with a locating boss corresponding to the shape of said embossment and a mounting surface surrounding said boss which corresponds to the replica surface.

2. The method of claim 1 including the formation of a bracket having a socket which intimately fits over said boss thereby to be oriented with respect to said fixture.

3. The method of claim 2 wherein said fixture and bracket are of metal, said securing said bracket to said fixture in the region of said boss and socket.

4. The method of claim 3 including limiting the size of said fixture in the area surrounding said boss to conform to the shape of a mounting base for said bracket, and weakening said fixture on a line of demarcation between such base and the remaining portion of said fixture whereby the base may be separated therefrom.

5. The method of claim 1 including the step of removing each fixture from the respective replica and embossment while retaining the formed shape thereof.

6. The method of claim 1 wherein forming said fixture includes electroplating onto said replica and embossment, and removing the fixture while retaining the formed shape thereof.

7. The method of claim 1 wherein forming said fixture includes magnetically forming a deformable sheet of metal onto said replica and embossment, and removing the fixture while retaining the formed shape thereof.

8. The method of claim 1 wherein said orienting embossment is in the form of an arch-shaped bar corresponding to the shape of said dental arch, affixing said bar to said dental arch against said surfaces of said replicas in registry with said locations, and forming said plate-like fixture over said bar.

9. The method of claim 8 including the step of making an impression of said dental arch with said bar mounted thereon, and forming a working cast from the impression, the tooth replicas having a reproduction of portions of said bar thereon;
   the fixture-forming step including electroplating onto discrete areas of the selected tooth replicas.

10. The method of claim 9 including limiting the size of each fixture in the area surrounding said boss to conform to the shape of a mounting base for a bracket.

11. The method of claim 5 or 10 including forming a bracket having a socket of a shape and size conforming to a sliding fit over said boss, fitting said bracket onto said boss and securing it to the underlying portion of said fixture.

12. The method of claim 9 including the step of sectioning the replicas from the model prior to the electroplating step.

13. The method of claim 1 wherein said locations on the dental arch are coplanar.

14. In a method of orthodontics for treating malocclusion, the steps of:
   (a) forming a model of the patient's teeth in the shape of a dental arch with the replicas of the teeth in idealized locations,
   (b) establishing on the labial and buccal surfaces of selected ones of said replicas locations for the mounting of brackets,
   (c) providing on each selected surface at the established location an orienting embossment,
   (d) forming onto the incisal edge and surface, including such embossment, in intimate conforming engagement, of each selected replica a plate-like fixture which has an exterior provided with a locating boss corresponding to the shape of said embossment and a mounting surface surrounding said boss which corresponds to the replica surface,
   (e) transferring each fixture to the corresponding tooth in the patient's mouth,
   (f) adhering the portion of said fixture immediately surrounding said boss to the tooth, and
   (g) separating from the tooth the incisal edge portion of the fixture leaving the remainder including the boss and the surrounding portion in the form of a mounting base for a bracket.

15. The method of claim 14 including the step of fitting a bracket onto the mounting base with said boss fitting into a complementary socket in said bracket.

16. The method of claim 15 including securing said bracket to said base.

17. The method of claim 14 including the step of providing a weakened section on said fixture between the incisal and base portions thereof, and separating the incisal edge portion at said weakened section.

18. The method of claim 14 wherein each fixture is formed by electroplating onto discrete portions of said model.

19. The method of claim 14 wherein each replica is sectioned from said model prior to forming said fixture, and forming the fixture on each selected replica by electroplating.

20. The method of claim 14 wherein said locations on said model lie in a common plane.

21. The method of claim 20 wherein said orienting embossment is in the form of a coplanar arch-shaped bar corresponding to the shape of the dental arch, affixing said bar to said dental arch and against said surfaces in registry with said locations, and forming each fixture over said bar to provide said boss.

22. The method of claim 21 including the step of forming a second model from the first model with said bar in place, and forming each fixture over the bar portions on the second replicas.

23. The method of claim 14 wherein said embossment is in the form of an elongated bar of orthogonal cross-section extending transversely of the replica.

24. The method of claim 23 including forming a bracket with a mounting surface having a socket therein which mates with said boss, fitting said bracket onto said base with said socket receiving said boss, and securing said bracket to said base.

25. The method of claim 24 wherein said locations are coplanar, forming wire-receiving slots in said brackets, said slots being so oriented with the respective sockets that said slots are aligned coplanar when the brackets are mounted in place.

26. Apparatus for locating a bracket on the labial or buccal surface of a patient's particular tooth comprising a custom formed and shape retentive plate-like fixture which intimately matches the shape including the irregularities of a portion of the incisal edge and labial or buccal surface of the tooth, said fixture being of substantially uniform thickness, the labial or buccal portion of the fixture serving as a mounting base for a bracket and having a bracket-locating and bracket-orienting portion thereon, the incisal edge portion of the fixture serving to locate said mounting base on and in registry with the corresponding labial or buccal surface and the irregularities thereof of the patient's tooth.

27. The apparatus of claim 26 wherein said fixture has a weakened section separating the incisal edge portion from the base portion.

28. The apparatus of claim 27 wherein said locating portion is a boss and is orthogonal in cross-section and elongated transversely of the tooth.

29. The apparatus of claim 26 including a bracket having a bottom surface provided with a portion which mates with said bracket-locating and bracket-orienting portion, said bottom surface being engageable with and secured to said base.

30. The method of fabricating an orthodontic appliance for use in repositioning one or more teeth in a patient's mouth, comprising the steps of:
  (a) forming a model of the patient's teeth in the shape of a dental arch with the replicas of the teeth in idealized locations,
  (b) forming onto the incisal edge and labial or buccal surface of each selected replica in intimate area-conforming engagement therewith a plate-like fixture,
  (c) establishing on each fixture a location for the mounting of a bracket and providing at said location a bracket-receiving and orienting means, and
  (d) mounting a bracket on the fixture and said means at such location.

31. The method of claim 30 wherein the locations on the fixtures lie in a common plane.

32. The method of claim 30 including the step of providing as said means a bracket orienting irregularity on said fixture at such location, and fitting such bracket having a mating portion to said irregularity.

33. The method of claim 32 wherein such irregularity is in the form of an orienting boss and securing such boss to said fixture.

34. The methiod of claim 32 wherein such irregularity is in the form of an orienting boss, indentation or opening in the fixture, and fitting such bracket having a mating portion to such boss, indentation or opening.

* * * * *